United States Patent [19]
Horn

[11] Patent Number: 5,848,700
[45] Date of Patent: Dec. 15, 1998

[54] EMERGENCY MEDICAL CARE KIT WITH MEDICAL EMERGENCY INSTRUCTIONS

[76] Inventor: Nathaniel Horn, 19110 Center Ave., Homewood, Ill. 60430

[21] Appl. No.: 916,803

[22] Filed: Aug. 22, 1997

[51] Int. Cl.⁶ ............................ B65D 69/00; B65D 85/00
[52] U.S. Cl. ........................ 206/570; 206/459.5; 206/572
[58] Field of Search ................................. 206/570–572, 206/370, 438, 459.5, 803; 220/524; 190/111

[56] References Cited

U.S. PATENT DOCUMENTS

| | | | |
|---|---|---|---|
| 611,136 | 9/1898 | Mason | 206/459.5 X |
| 1,480,865 | 1/1924 | Slade | 206/570 |
| 1,487,014 | 3/1924 | Davis | 206/570 |
| 1,644,830 | 10/1927 | Henderson | 206/572 X |
| 1,727,235 | 9/1929 | Joyse, Jr. | 206/572 |
| 2,999,583 | 9/1961 | Mancini | 206/459.5 X |
| 4,230,226 | 10/1980 | Boe | 206/570 |
| 4,513,866 | 4/1985 | Thomas | 206/570 |
| 4,828,113 | 5/1989 | Friedland et al. | 206/570 |
| 5,011,020 | 4/1991 | Stevens et al. | 206/570 |
| 5,207,303 | 5/1993 | Oswalt et al. . | |
| 5,447,237 | 9/1995 | Carter et al. . | |
| 5,515,974 | 5/1996 | Higson . | |
| 5,544,753 | 8/1996 | Monica . | |

FOREIGN PATENT DOCUMENTS 2644341  9/1990  France ................................. 206/370

*Primary Examiner*—Byron P. Gehman
*Attorney, Agent, or Firm*—Henderson & Strum

[57] ABSTRACT

An emergency medical kit includes a carrying case of approximately briefcase or small suitcase size with the upper and lower sections divided into a large number of compartments by insertion of a plastic organizer. Each compartment is directed to a particular medical emergency and is so identified on its cover or lid. The reverse side of the compartment cover has instructions for treating the particular emergency, while the compartment contains the necessary care items for that particular emergency. A divider is held by snaps across the upper section of the case to help contain the contents and also provides instruction for use of the kit, some general first aid information, and a list of emergency telephone numbers.

3 Claims, 1 Drawing Sheet

EMERGENCY MEDICAL CARE KIT WITH MEDICAL EMERGENCY INSTRUCTIONS

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

1. Field of the Invention

This invention relates to emergency medical kits.

2. Description of the Related Art

Emergency medical care kits are well known in the art and generally comprise a container or case which contains a number of medical care items such as bandages, compresses, wraps, cervical collars, chemical hot and cold packs, tourniquets, tapes, antiseptics and analgesics, scissors, tweezers, cotton swabs, and a First Aid manual. They are not particularly well suited for quick use in an emergency by a layman with little or no training or experience in medical care inasmuch as such care would require first finding the injury and necessary procedure in the manual, then finding the proper equipment and care items, and finally attempting to provide the necessary care.

BRIEF SUMMARY OF THE INVENTION

Briefly stated, the emergency medical care kit that forms the basis of the present invention comprises a carrying case approximately the size of a briefcase or small suitcase with the upper and lower sections divided into a large number of compartments by insertion of a plastic organizer with removable covers. Each compartment is directed to a particular medical emergency and is so identified on its cover. The reverse side of each compartment cover has instructions for treating the particular emergency, while the compartment itself contains the necessary care items for that particular emergency. A hinged divider is held by snaps across the upper section of the case to help contain the contents and also provides instruction for use of the kit, some general first aid information, and a list of emergency telephone numbers.

BRIEF DESCRIPTION OF THE SEVERAL VIEWS OF THE DRAWINGS

Other objects, advantages, and novel features of the present invention will become apparent from the following detailed description of the invention when considered in conjunction with the accompanying drawings, wherein.

DETAILED DESCRIPTION OF THE INVENTION

Figure 1:
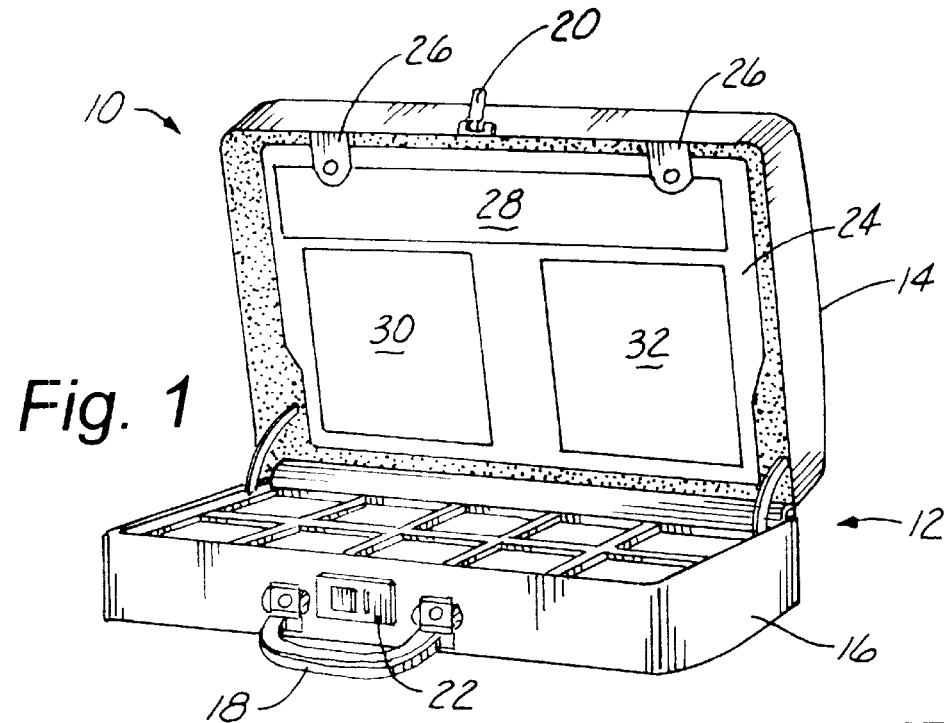
FIG. 1 is a perspective view of the invention.

Referring now to the drawings, wherein like reference numerals designate identical or corresponding parts throughout the several views, FIG. 1 shows the invention depicted generally at 10 which is seen to comprise a carrying case 12 having an upper section 14 hinged to a lower section 16, a carrying handle 18 and a latch 20 and lock 22. The upper section further includes a partition 24 pivotally attached to the upper section 14 near the case hinge line and secured across the upper section 14 by snaps tabs 26. The surface of the partition 24 is divided into several areas 28, 30, 32 which provide information on the use of the invention as well other useful information such as emergency telephone numbers.

Figure 2:
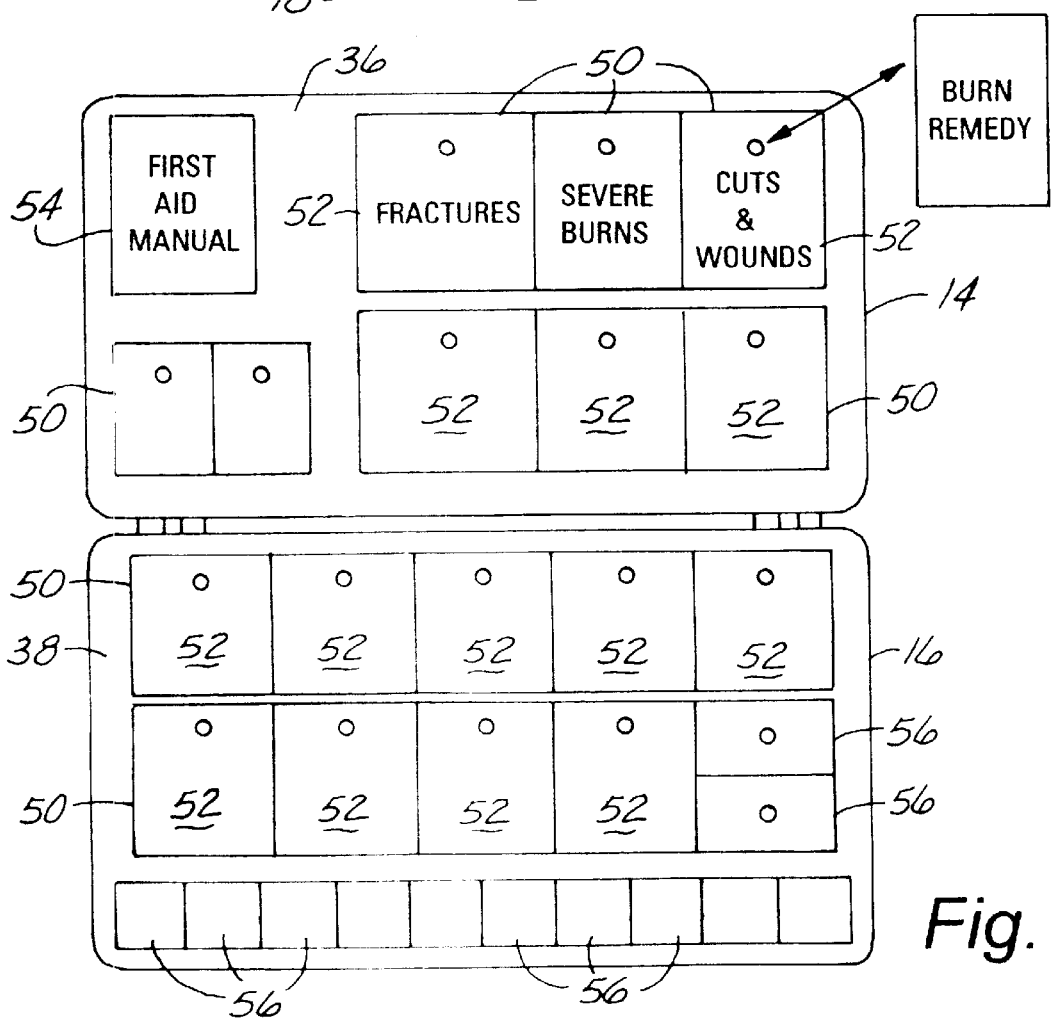
FIG. 2 is a top plan view of the invention in the open configuration.

Referring also now to FIG. 2, it can be seen that the upper section 14 and lower section 16 each contain an organizer unit 36, 38 which divides the sections into a plurality of separate compartments. A majority of the compartments 50 have covers 52 removably affixed over the individual compartments 50 and which recite a particular medical emergency on their front side. For example, one such cover 52 might read "Severe Burns" while a second might read "Cuts and Wounds" and a third might read "Fractures". On the reverse side of each particular cover 52 are instructions for treating the medical condition recited on the front. Finally, contained within each particular compartment 50 are the necessary medical supplies for treating the condition described on the cover. For example, within the "Severe Burns" compartment may be burn ointments, sterile wraps, and pain medication; while in the "Cuts and Wounds" compartment may be bandages, tape, antiseptics and a tourniquet. One of the compartments 54 will preferably contain a First Aid Manual, while some of the compartments 56 may contain commonly used supplies such as gauze pads, tape, and band aids.

It should therefore be clear that this invention greatly aids a layman in providing emergency medical care in a timely fashion since the instructions for care and the necessary supplies are readily identified and available. Also readily available are telephone numbers and other information for obtaining qualified medical care as quickly as possible.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

What is claimed is:

1. An emergency medical care kit, comprising:

(a) a hard walled carrying case having first and second concave sections hingedly connected along a first edge of each section and including a handle and a closing latch;

(b) a first organizer unit, secured within said first concave section, whereby said first section is divided into a plurality of compartments;

(c) a second organizer unit, secured within said second concave section, whereby said second section is divided into a plurality of compartments;

(d) covers for a plurality of said compartments, wherein each of said covers has a front side selectively reciting a particular medical emergency and a reverse side bearing instructions for treating said particular medical emergency; wherein the particular medical emergency on each of said covers is different; and (e) medical supplies, selectively contained within a plurality of said compartments, which are appropriate for treatment of the selected medical emergency recited on the cover of each compartment.

2. The emergency medical care kit as recited in claim 1 and further comprising a partition, removably secured upon said second concave section providing information for use of the emergency medical care kit and emergency telephone numbers.

3. The emergency medical care kit as recited in claim 2 and further comprising a first aid manual contained within one of said compartments.

* * * * *